United States Patent
Sarvazyan et al.

(10) Patent No.: US 7,587,291 B1
(45) Date of Patent: Sep. 8, 2009

(54) FOCUSING OF BROADBAND ACOUSTIC SIGNALS USING TIME-REVERSED ACOUSTICS

(75) Inventors: Armen P. Sarvazyan, Lambertville, NJ (US); Laurent Fillinger, Pulversheim (FR); Alexander Sutin, Summit, NJ (US)

(73) Assignee: Artann Laboratories, Lambertville, NJ (US)

( * ) Notice: Subject to any disclaimer, the term of this patent is extended or adjusted under 35 U.S.C. 154(b) by 0 days.

(21) Appl. No.: 12/115,240

(22) Filed: May 5, 2008

(51) Int. Cl.
*G01K 11/00* (2006.01)
*A61B 5/05* (2006.01)

(52) U.S. Cl. ...................... 702/103; 600/407

(58) Field of Classification Search .......... 702/103, 702/104, 106, 138–139, 189–191, 193–195, 702/198; 367/2, 7; 73/584, 586–587, 602, 73/628–629, 632, 645, 646; 181/123, 125, 181/139, 142, 175; 600/407
See application file for complete search history.

(56) References Cited

U.S. PATENT DOCUMENTS

| | | | |
|---|---|---|---|
| 5,092,336 A * | 3/1992 | Fink | 600/443 |
| 5,207,214 A * | 5/1993 | Romano | 601/4 |
| 5,590,657 A * | 1/1997 | Cain et al. | 600/439 |
| 5,613,940 A * | 3/1997 | Romano | 601/2 |
| 5,762,066 A | 6/1998 | Law et al. | |
| 5,769,790 A | 6/1998 | Watkins et al. | |
| 6,128,958 A | 10/2000 | Cain | |
| 6,488,630 B1 | 12/2002 | Hand et al. | |
| 6,490,469 B2 * | 12/2002 | Candy | 600/407 |
| 2004/0162507 A1 | 8/2004 | Govari et al. | |
| 2004/0162550 A1 | 8/2004 | Govari et al. | |

FOREIGN PATENT DOCUMENTS

EP 1449564 A1 * 8/2004

OTHER PUBLICATIONS

Choi et al., Formation of Desired Waveform and Focus Structure by Time Reversal Acoustic Focusing System, 2006 IEEE Ultrasonics Symposium, pp. 2177-2181.*
O'Neil, H.T., Theory of Focusing Radiators, Sep. 1949, J. Acoust. Soc. Am., vol. 21, No. 5, pp. 516-526.*
Ebbini et al., A Spherical-Section Ultrasound Phased Array Applicator for Deep Localized Hyperthermia, Jul. 1991, IEEE Transactions on Biomedical Engineering, vol. 38, No. 7, pp. 634-643.*

(Continued)

*Primary Examiner*—Michael P. Nghiem
*Assistant Examiner*—Toan M Le
(74) *Attorney, Agent, or Firm*—Boris Leschinsky (57) ABSTRACT

A method for focusing broadband acoustic signals with flat spectral content based on Time-Reversed Acoustics (TRA) principle is disclosed. The method of the invention differs from the conventional TRA focusing in that it includes an additional step of adjusting the spectral content of time-reversed signal, prior to applying it to the radiating transducer. This additional step, which includes attenuation of the spectral components with high amplitude and amplification of the spectral components with low amplitude, leads to flattening of the spectra of the radiated signal and widening of its frequency band. TRA focusing with this additional step of adjusting spectral content of the radiated signal allows generation of shorter pulses and provides better concentration of acoustic energy than standard TRA focusing.

7 Claims, 9 Drawing Sheets

OTHER PUBLICATIONS

Folegot et al., Adaptive Instant Record Signals Applied to Detection With Time Reversal Operator Decomposition, Jun. 2005, J. Acoust. Soc. Am., vol. 117, No. 6, pp. 3757-3765.*

Montaldo et al., Generation of Very High Pressure Pulses With 1-Bit Time Reversal in a Solid Waveguide, Dec. 2001, J. Acoust. Soc. Am., vol. 110, No. 6, pp. 2849-2857.*

Laurent Fillinger, Alexander Sutin, Armen Sarvazyan, Time Reversal Focusing of Short Pulses, Proceedings of 2007 IEEE Ultrasonics Symposium, pp. 220-223.

Fink M. Time-Reversed Acoustics. Scientific American, Nov. 1999, pp. 91-97.

* cited by examiner

FOCUSING OF BROADBAND ACOUSTIC SIGNALS USING TIME-REVERSED ACOUSTICS

FIELD OF THE INVENTION

The present invention relates generally to a method for generating and focusing broadband acoustic signals for various industrial and medical applications. More specifically, it relates to medical imaging, surgery and therapy methods where there is a demand for high intensity focused short ultrasonic pulses. Other applications of the method of invention include non-destructive testing based on detection of defects altering the spectrum of received acoustic signals and detection of buried objects using seismic acoustic waves.

BACKGROUND OF THE INVENTION

Focusing of short acoustic pulses is a fundamental aspect of most of the medical and industrial applications of ultrasound. In medical imaging, the quality of focusing of acoustic waves is directly related to such an important parameter of imaging as its spatial resolution. In therapeutic and surgical applications, effective focusing of ultrasound is important for delivering sufficient amount of acoustic energy to a target tissue to achieve necessary biological effect as well as for selective action on the lesion which needs to be treated without damaging surrounding healthy tissues. The use of focused ultrasound in medicine is described in detail in various patents as listed below (these patents are all incorporated herein in their entirety by reference): U.S. Pat. Nos. 5,207,214; 5,590,657; 5,613,940; 5,762,066; 5,769,790; 6,128,958; and 6,488,630.

Conventional approaches to focusing acoustic waves include geometrical focusing and electronic focusing. Geometrical focusing is based on the use of a transducer manufactured as a spherical shell or acoustic lenses (O'Neil, H. T. "Theory of focusing radiators". J. Acoust. Soc. Am. 1949, 21, pp. 516-526). Geometrical focusing systems are simple, inexpensive and easy to make, but their principal disadvantage is that they have the fixed focal distance and could not steer the focus along and off the axis. The electronic focusing is based on the use of phased-array systems consisting of a number of separate elements (Ebbini E. S., Cain C. A. "A spherical-section ultrasound phased-array applicator for deep localized hyperthermia". IEEE Trans. Biomed. Eng. 1991 V. 38. No. 7. pp. 634-643). Each element is excited by its own circuit that allows changing in a controllable way of the phase relationships over the array aperture, therefore creating any desired shape of a wave front.

An alternative technique of focusing ultrasonic waves is based on principles of Time-Reversed Acoustics (TRA) which were developed by M. Fink ("Time Reversed Acoustics", Physics Today, March 1997, pp. 34-40, and Fink M. "Time reversed acoustics". Scientific American, pp. 91-97 (1999), both of these articles are incorporated herein by reference). The TRA technique is based on the reciprocity of acoustic propagation, which implies that the time-reversed version of an incident pressure field naturally refocuses on its source. U.S. Pat. No. 5,092,336 to Fink, which is also incorporated herein by reference, describes a TRA device for focusing of acoustic waves in tissues.

Several practical examples of TRA ultrasound focusing system are described in the U.S. patent application Ser. No. 10/370,134 (U.S. Patent Application Publication No. 2004/0162550), now U.S. Pat. No. 7,201,749, and U.S. patent application Ser. No. 10/370,381 (U.S. Patent Application Publication No. 2004/0162507), now abandoned, to Govari et al. as well as his counterpart European Patent Application No. EP 1449564, all of which are incorporated herein by reference.

The bandwidth of the probes generating ultrasound is mainly defined by the bandwidth of the transducers employed in the probe. These transducers are typically made in the form of discs and plates of piezoelectric materials of certain constant thickness, which defines resonance frequencies of the transducer. Ultrasound is radiated near resonance frequencies much more efficiently than at other frequencies. Use of resonant transducers limits the possibility to generate short pulses since the shorter is the pulse the wider is its spectrum. The pulse cannot be made much shorter than the ringing time of the transducer. Transducers resonance frequencies dominate in the spectrum of the focused signal. A possibility of increasing the bandwidth of the TRA focusing system is described in our co-pending patent application Ser. No. 12/036,531 filed Feb. 25, 2008 and entitled "Broadband Ultrasonic Probe", which is incorporated herein by reference in its entirety. This possibility is based either on the use of broadband piezotransducers with variable thickness or on the simultaneous use of several transducers having different resonance frequencies. Generation of short pulses as well as a signal with arbitrary predetermined waveforms requires not only a wide spectral bandwidth of the focusing system but also sufficient flatness of that spectrum.

There is a need therefore for acoustic focusing methods which combine the advantages of the broad frequency band and the flatness of the frequency bandwidth. The invention described hereinafter meets such a need.

SUMMARY OF THE INVENTION

Accordingly, it is an object of the present invention to provide a TRA method of focusing acoustic waves with a broad and flat spectral content. The method of the invention includes an additional step of adjusting the spectral content of time-reversed signal, prior to applying it to the radiating transducer. This additional step, which includes attenuation of the spectral components with high amplitude and amplification of the spectral components with low amplitude, leads to flattening of the spectra of the radiated signal and widening of its frequency band. TRA focusing with this additional step of adjusting spectral content of the radiated signal allows generation of shorter pulses and provides better concentration of acoustic energy than standard TRA focusing. There are two alternatives of adjusting spectral content of time-reversed signal used for focusing acoustic wave. One alternative is based on experimentally obtaining the spectrum-adjusted signal and the second alternative includes numerical computation to achieve the same goal.

It is also an object of the invention to provide an experimental method of obtaining spectrum-adjusted time-reversed signal by additional steps of designing a spectrum adjusted emission signal from the power spectrum density of the recorded response to the linear frequency sweep signal, emission of that spectrum adjusted signal, and recording of the response to that emission.

It is another object of the present invention to provide a numerical computation method of obtaining the spectrum adjusted time-reversed signal which includes determination of the impulse response from emitter to receiver, the elaboration of a filter based on the power spectrum density of the recorded response to the emitted signal, application of that filter to the emitted signal and convolution of that filtered signal with the determined impulse response.

It is a further object of the invention to allow using the method of TRA focusing with frequency orthogonal signals for reducing the time for elaboration of time-reversed focusing signals when using a TRA focusing system with several channels.

It is also an object of the invention to produce focused signal with higher amplitude by emitting ternary signals. The ternary signals are formed by transformation of amplitude of the conventionally emitted signals to three discrete values (minimum, zero and maximum). The phase information is preserved while the energy content is increased, thus leading to higher amplitude of focused waves.

BRIEF DESCRIPTION OF THE DRAWINGS

A more complete appreciation of the subject matter of the present invention and various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
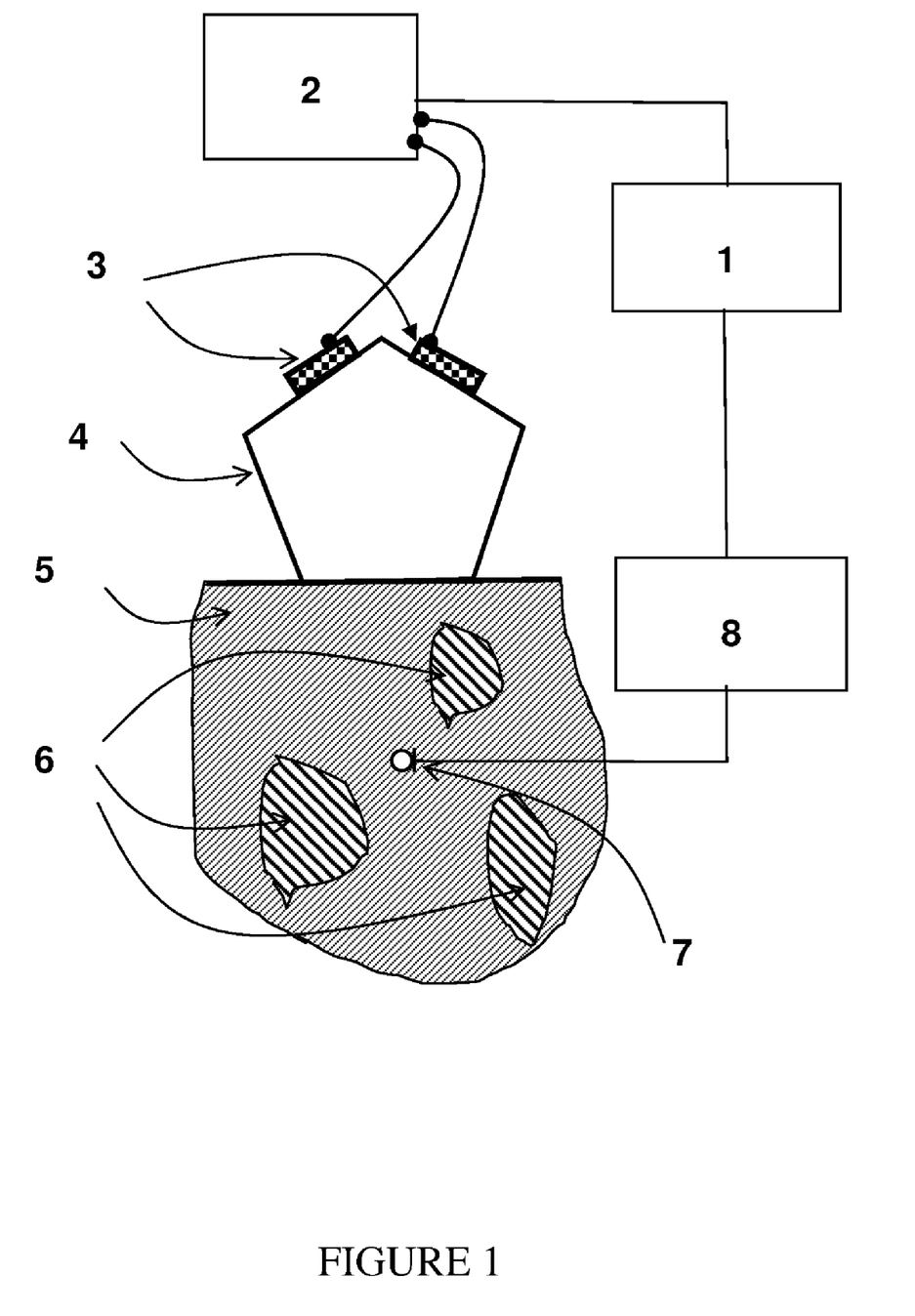
FIG. 1 is a general diagram illustrating main components of a TRA system for focusing of acoustic waves.

FIG. 1 is a general diagram showing various elements of a setup for focusing acoustic waves with the principle of Time Reversal Acoustics. The electrical signals from electronic unit 1 are amplified by the power amplifier 2 and applied to radiating transducers 3. Each radiating transducer 3 is preferably operated independently. Radiating transducer 3 can be made from a piezoelectric crystal, or using piezo-ceramic or piezo-composite material. The radiating transducers 3 are acoustically coupled to a reverberator 4, which is itself coupled to a propagating medium 5. The acoustic wave emitted by the radiating transducers 3 is reflected/scattered within the reverberator 4 and further inside the propagating medium 5, which can include inhomogeneities 6. An acoustic sensor 7 such as a hydrophone is placed inside the propagating medium 5 and allows measurement of the acoustic signal at the point where it is placed. A short acoustic pulse generated by the radiating transducer after multiple reflections in the reverberator 4 as well as in the medium 5, will be detected by the sensor 7. The electrical signal from the sensor 7 is then amplified by the preamplifier 8 and sent to the electronic unit 1, where it is time-reversed and stored in memory.

TRA focusing is realized by emitting a properly designed focusing acoustic signal(s) that will generate acoustic waves focused at a desired location. The TRA focusing system can involve one or more emitting radiating transducers, each of which requires application of a specifically designed focusing acoustic signal. Those signals have to be designed before the operation of the system for focusing. The design of these signals is conventionally a three step procedure, as presented in FIG. 2, involving an emission, a reception and a processing. The designed signals then have to be stored in the memory of the electronic unit 1 (or the computer that controls it) for subsequent use, that is for obtaining TRA focused acoustic wave by simultaneous emission of the stored signals.

Figure 2:
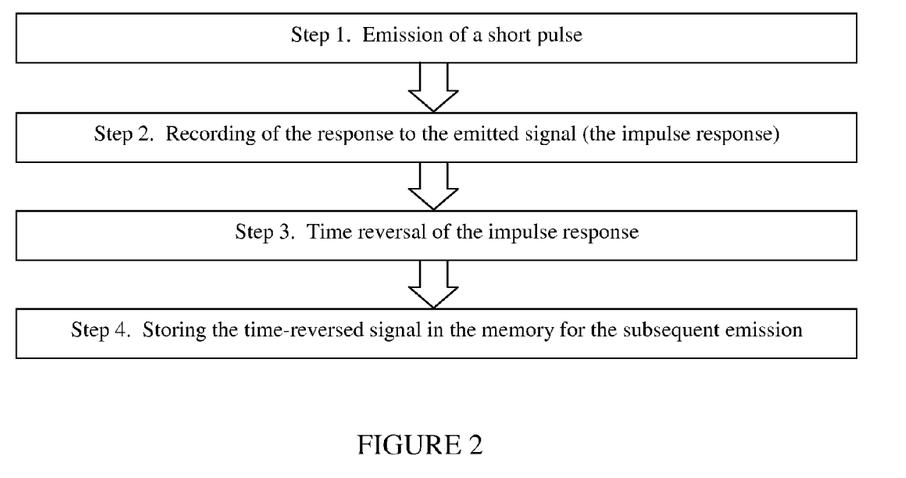
FIG. 2 is a block-diagram presenting the steps for a conventional Time-Reversal focusing procedure.

Traditionally, to obtain focused acoustic waves at a given location, a sensor 7 has to be initially placed at that location. The first step is to emit an initial short acoustic pulse from a radiating transducer 3. This emission produces unfocused acoustic waves that propagate throughout media 5. In step 2, the response to that initial emission is recorded on the sensor 7. Because the emitted signal is a pulse, the recorded response is the "impulse response". Step 3 consists of determination of the signal that will lead to focusing at the position of the sensor 7 when supplied to the radiating transducer 3. This signal is called "focusing signal". According to the principles of time-reversal acoustics, the focusing signal is the time-reversed impulse response from the radiating transducer 3 to the sensor 7. Step 4 is the storing of the designed focusing signal in the memory for subsequent use.

However, as the emitted initial short pulse does not carry much energy, the signal recorded in step 2 can be relatively noisy, thus limiting the performance of subsequent focusing. Another type of emission signal having much longer duration is therefore preferably used in step 1. This alternative realization of the conventional TRA focusing method is presented in FIG. 3.

In step 1, the emission of short acoustic pulse is replaced by the emission of a linear frequency sweep, which is a sinusoidal signal whose frequency evolves linearly with time. Because this signal lasts longer than the short pulse, it carries more energy so that the recorded response signal in step 2 is less polluted by noise. In step 3, the impulse response is determined by cross-correlation of the emitted linear frequency sweep signal with the response on the sensor 7 to the emission of the linear frequency sweep. In step 4, the computed impulse response is then time-reversed, leading to the desired focusing acoustic signal. Step 5 includes storing the designed signal for subsequent use. When the time-reversal focusing system includes more than one radiating transducer 3, this general procedure as shown on FIG. 2 or FIG. 3 has to be repeated for each radiating transducer.

Once the focusing acoustic signal stored in memory (see the last step of the procedure illustrated in FIG. 3) is emitted from the corresponding radiating transducer 3, focused acoustic waves are obtained at the position of sensor 7. If the time-reversal focusing system contains several radiating transducers 3, each transducer should emit its associated signal at the same time as others. As the radiating signals have been determined in the previously described steps, the presence of the sensor 7 is no longer necessary.

The present invention calls for additional steps in obtaining the focusing acoustic signal. In the most general sense, the additional steps include spectral adjustment of the focusing signals by attenuation of the spectral components with high amplitude and amplification of the spectral components with low amplitude, leading to flattening of the spectra of the radiated signal and widening of its frequency band. There are two alternatives of adjusting spectral content of time-reversed signal used for focusing acoustic wave. One alternative is based on experimentally obtaining the spectrum-adjusted signal and the second alternative includes numerical computation to achieve the same goal.

Figure 3:
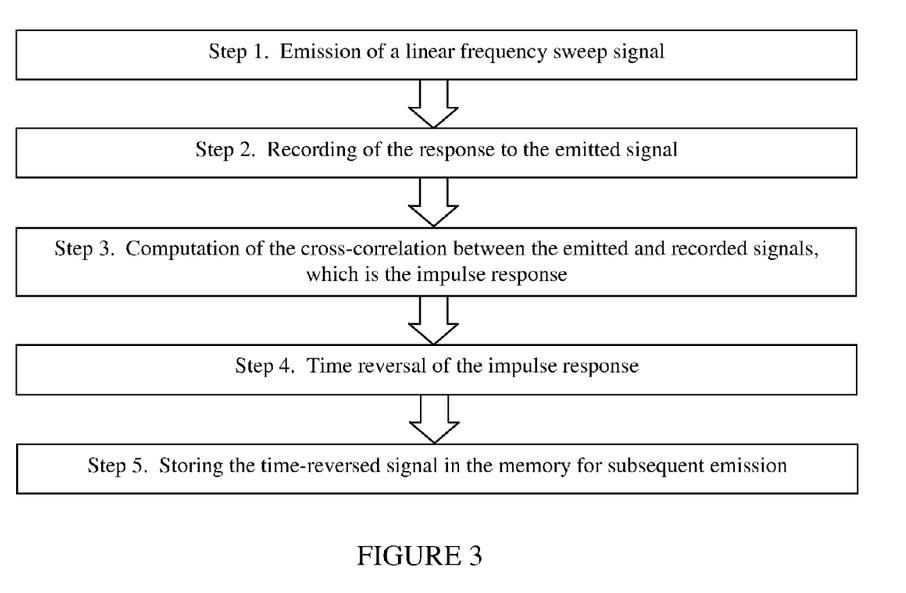
FIG. 3 is a block-diagram presenting the steps for an alternative, more robust, but still conventional Time-Reversal focusing procedure.
Figure 4:
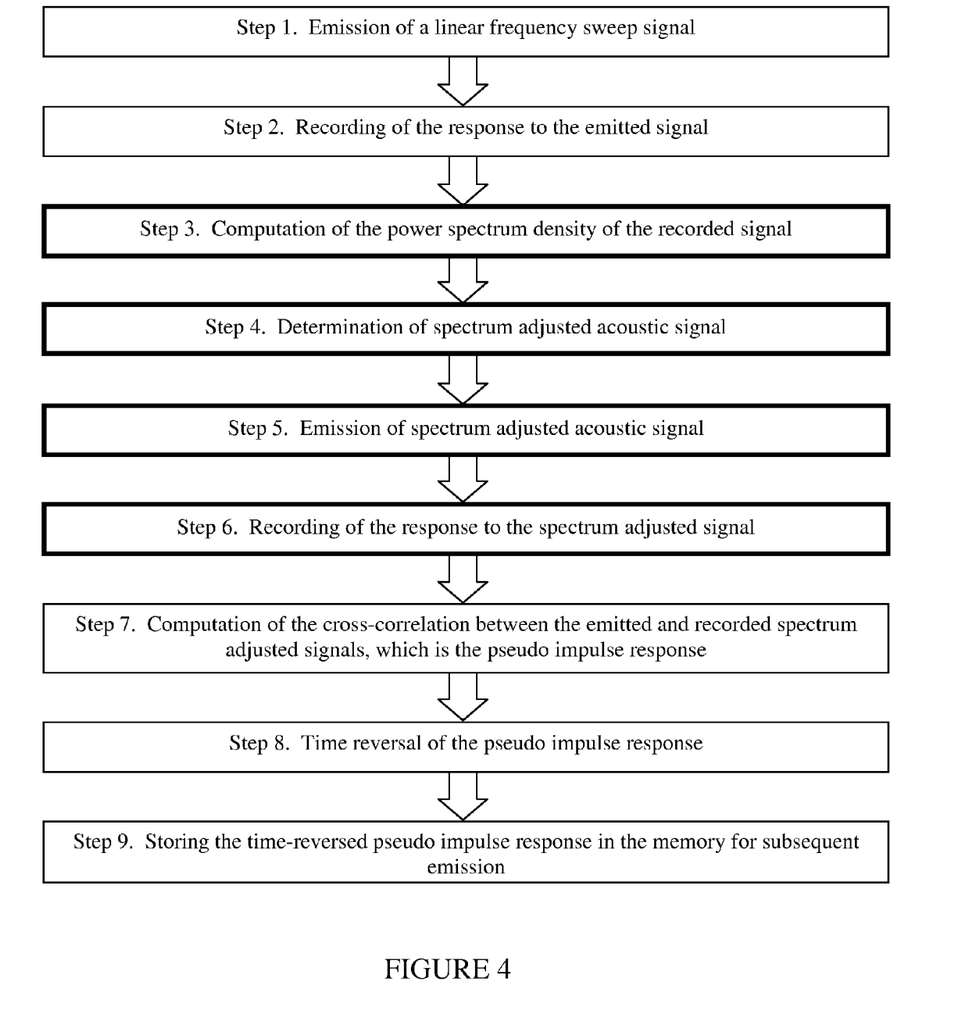
FIG. 4 is a block-diagram presenting the steps for a Time-Reversal focusing procedure according to the first aspect of the present invention, novel steps are highlighted in bold frames.

FIG. 4 shows a general diagram illustrating the method of the first aspect of the present invention. The traditional procedure described in FIG. 3 is expanded by additional steps (shown in bold frames in FIG. 4) after recording of the response to the initial emitted broadband signal. Step 3 is the first additional step. It consists of the computation of the power spectrum density of the recorded signal. This power spectrum density allows determination of spectral components with high and low amplitudes. It is used in step 4 to determine the spectrum-adjusted acoustic signal which is then emitted from radiating transducer 3 in step 5. Step 6 consists of the recording the received spectrum-adjusted signal by sensor 7. As a consequence of the frequency adjustment of the emitted spectrum-adjusted signal, the response of step 6 has more uniform spectrum than the response of step 2. Following steps are performed according to the conventional procedure. Step 7 consists in the computation of the cross-correlation between the emitted and recorded spectrum-adjusted signals. Because of the frequency adjustment, the result is not the impulse response and will be referred to as pseudo-impulse response. This pseudo-impulse response is time reversed in step 8, and the time reversed focusing signal is then stored in step 9 for further TRA focusing.

Frequency adjustment may be accomplished in a number of ways. One of the preferred ways to do so is to adjust the frequency content by modifying the sweep rate of the frequency change while keeping the signal amplitude constant. The sweep rate at a given frequency is preferably selected to be proportional to the power spectrum density of the recorded response to the emitted linear frequency sweep signal.

Another preferred method is to keep the sweep rate of the signal constant while modulating its amplitude. In this case, the amplitude is preferably selected to be inversely proportional to the square root of the power spectrum density of the recorded response to the emitted linear frequency sweep.

In both described methods, a predetermined threshold is used as a control parameter in order to limit the range of sweep rate or the amplitude change. This threshold parameter enables controlling of a balance between widening and flattening of the spectrum of focused acoustic waves.

Figure 5:
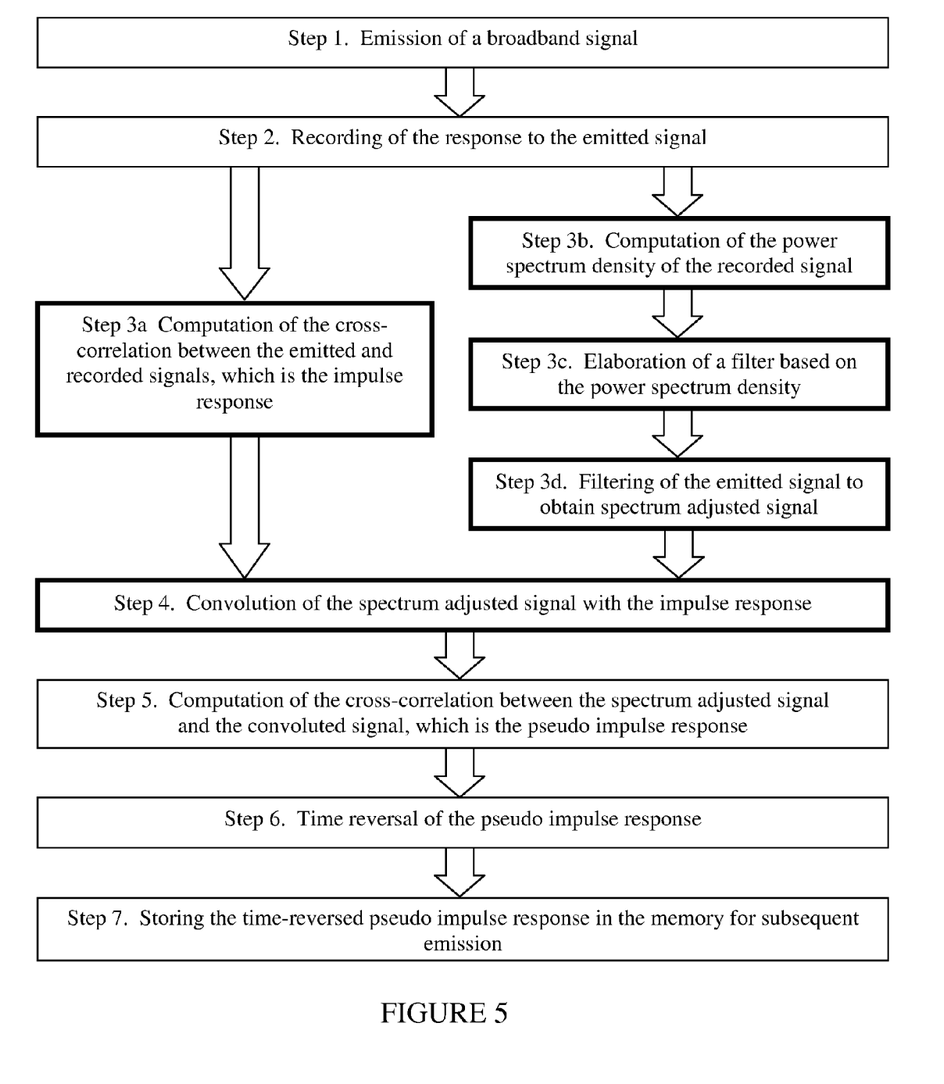
FIG. 5 is a block-diagram presenting the steps for a Time-Reversal focusing procedure according to the second aspect of the present invention, novel steps are highlighted in bold frames.

FIG. 5 shows the second aspect of the present invention with an alternative procedure to that of FIG. 4 where the additional steps of frequency adjustment are performed using numerical computation instead of experimentally. Again, modified steps appear in bold frames. In the left branch (step 3*a*), the impulse response from the radiating transducer 3 to the sensor 7 is numerically computed by cross-correlation to simulate propagation and recording of a signal determined in the other branch (steps 3*b* to 3*d*). In step 3*b*, the power spectrum density of the response to the emitted signal is computed. It is used for elaboration of a numerical filter in step 3*c*. In step 3*d*, this filter is applied to the emitted signal of step 1, providing the calculation of a filtered spectrum-adjusted signal, which is the numerical analog of the experimentally obtained spectrum-adjusted frequency signal of FIG. 4. Propagation of this spectrum-adjusted signal and recording of its spectrum-adjusted response by the sensor 7 is then numerically simulated in step 4 by convolution of the spectrum-adjusted signal of step 3*d* with the impulse response computed in step 3*a*. The spectrum-adjusted signal and its simulated response are then used in step 5 to compute the pseudo-impulse response by cross-correlation. This signal is subsequently time-reversed in step 6, leading to the final focusing signal which is stored in step 7.

As described above, the emitted signal and its recorded response signal are used for two purposes. The first purpose is to determine the impulse response. The second purpose is to define a filter having a response at a given frequency being inversely proportional to the square root of power spectrum density of the initial impulse response signal. When this filter is applied to the emitted signal, a spectrum-adjusted signal is produced which is a computed analog to the spectrum-adjusted sweep signal of the first aspect of the invention. The found impulse response is then used to simulate the propagation of that filtered signal, therefore obviating the need to emit it experimentally.

Since there is no need to physically repeat the focusing procedure for the second time using the spectrum-adjusted signal, this method allows for faster completion of the TRA-based focusing procedure of the invention.

Another advantage of the second aspect of the invention is that this numerical simulation method can be applied to any arbitrary acoustic signal. Therefore, the emitted acoustic signal in step 1 of FIG. 5 can be any type of a broadband signal, including but not limited to a short pulse, a linear frequency sweep and a broadband "noise" signal.

A further useful improvement of the method according to the second aspect of the invention is using the emitted signals of step 1 with orthogonal frequency content, such signals are described in T. Folegot, J. DeRosny, C. Prada and M. Fink, "Adaptive instant record signals applied to detection with time reversal operator decomposition", J. Acoust. Soc. Amer. 117, pp. 3757-3765, 2005, incorporated herein by reference in its entirety. This method is useful when a time-reversal system with more than one channel is used. Orthogonal signals include signals whose frequency contents do not overlap. The method in FIG. 5 is fully applicable to orthogonal signals and presents an important advantage since the described focusing procedure can be performed simultaneously on all emitting channels. This results in a faster determination of the focusing signal than when the procedure is applied successively to one channel at a time.

Figure 6:
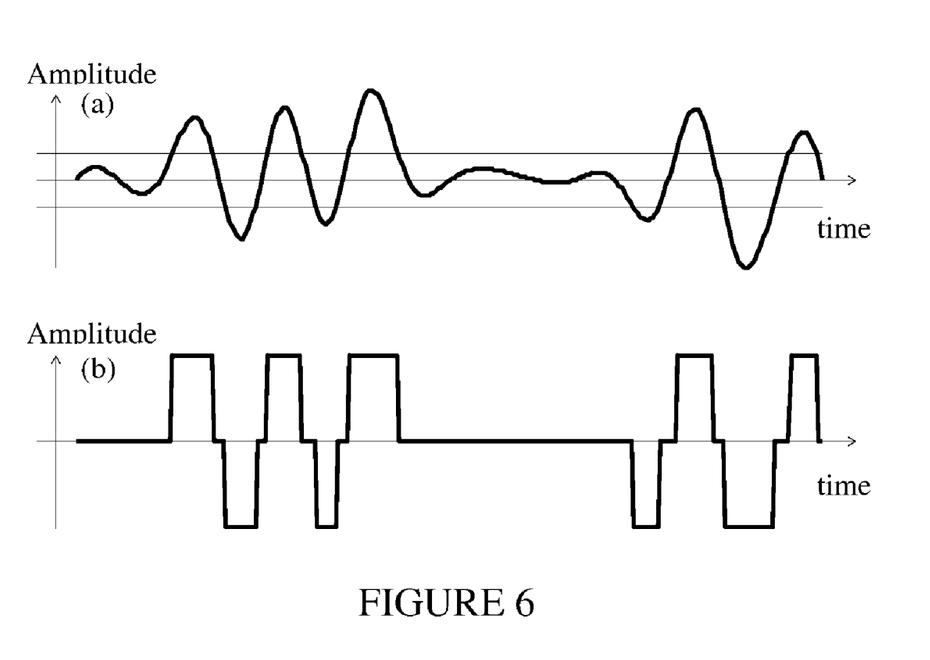
FIG. 6 illustrates how a ternary signal (b) is deduced from an arbitrary signal (a)

A further yet improvement of the method of the invention includes using a ternary transformation, which includes an additional processing step applied to the focusing signals before emission. This processing can be applied to the focusing signal determined by any of the above described methods and it presents an improvement of binary transformation as suggested in Montaldo C., Roux P., Derode A., Negreira C., Fink M. "Generation of very high pressure pulses with 1-bit time reversal in a solid waveguide". J. Acoust. Soc. Am., 2001, 110, 6, pp. 2849-2857, incorporated herein in its entirety by reference. Instead of presenting a large range of values, the emitted signal is transformed to have only three values, depending on the values of the pre-processed signal, as determined by any of the described above procedures. An example of this processing is presented in FIG. 6. An arbitrary signal is shown in (a) along with dashed lines having levels corresponding to the predetermined threshold and to its opposite. The ternary signal associated with signal (a) is presented as signal (b). The values of the signal (a) between the dashed lines are replaced by 0 while values out of that range are set to maximum or minimum values, depending on their sign. The use of the ternary mode allows an increase of the amplitude of the focused acoustic waves. Appropriate choice of the threshold value allows benefit from maximum amplification while limiting the influence of noise.

Example of Using the Method of the Invention

Figure 7A:
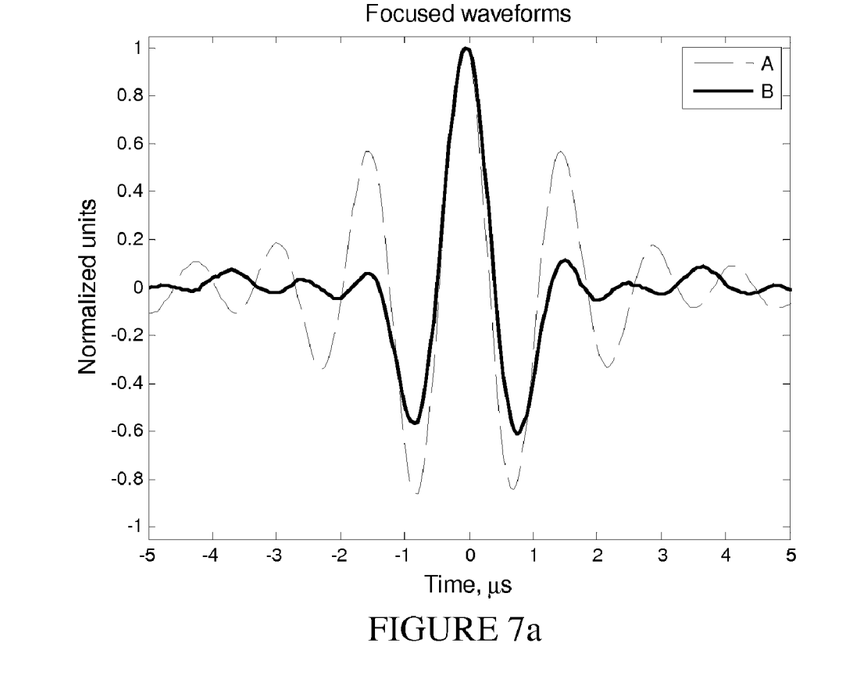
FIG. 7a is a graph showing a focused waveform obtained with the conventional method (A) and with a method of the present invention (B) and FIG. 7b presents the focused signal waveform bandwidth and amplitude as function of the threshold.
Figure 7B:
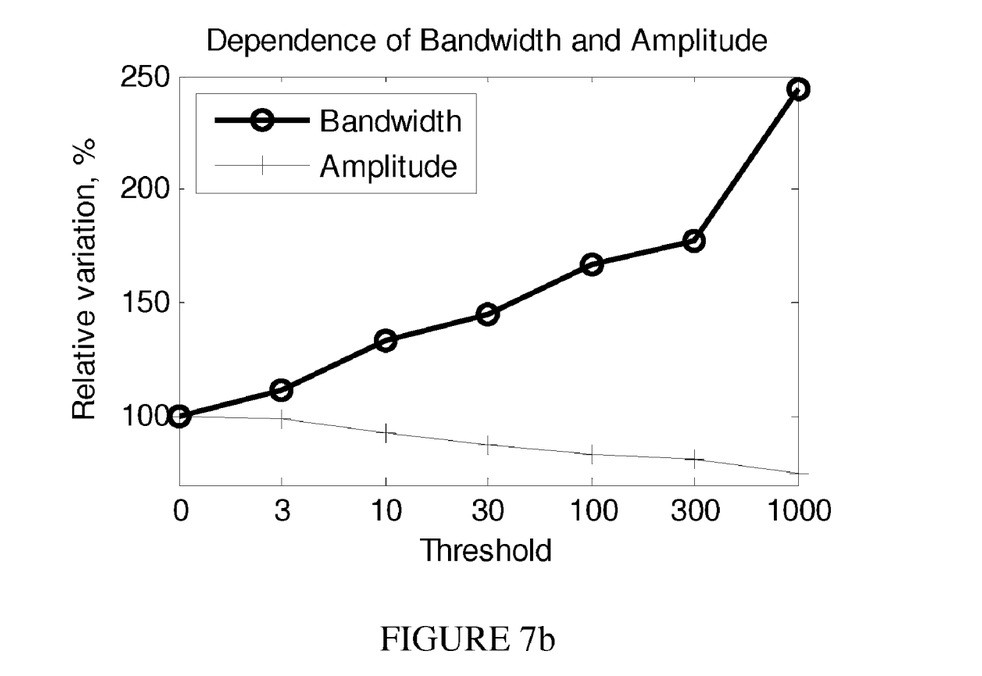

FIG. 7a shows focused waveforms obtained in one of our experimental set-ups with the conventional time-reversal technique (dashed line A) and with the proposed technique using amplitude modulated sweep (solid line B). The reduction of focused wave duration obtained with the method of the present invention is evident. The shortening of the waveform duration is a result of significant increase of the focusing system bandwidth and is also accompanied by a minor decrease of signal amplitude. These dependences of the bandwidth and the amplitude on the modulation threshold are shown in FIG. 7b.

Figure 8A:
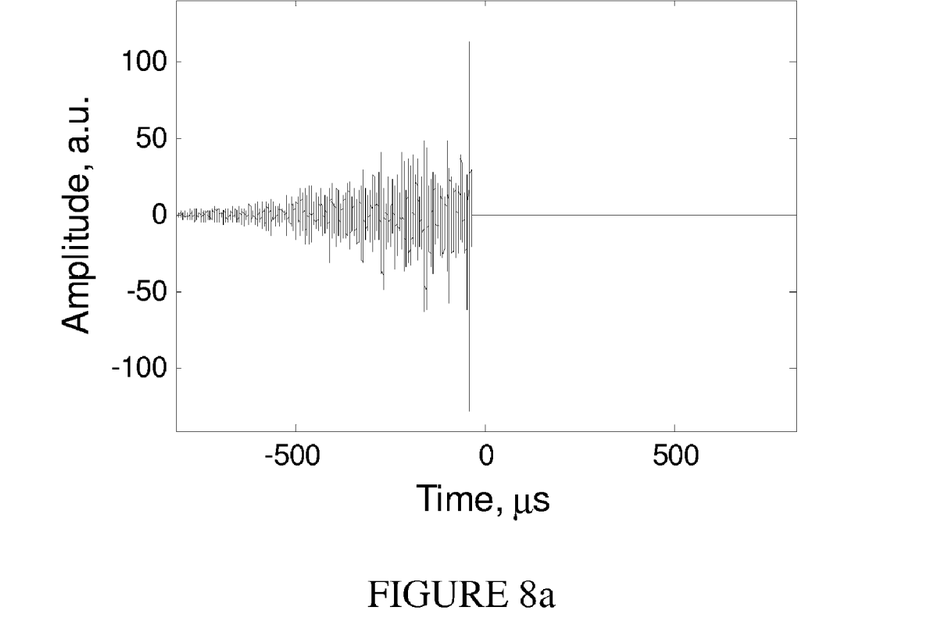
FIGS. 8a through 8c are graphs illustrating a TRA focusing procedure using a non-uniform frequency sweep and responses thereto when associated with a ternary mode.
Figure 8B:
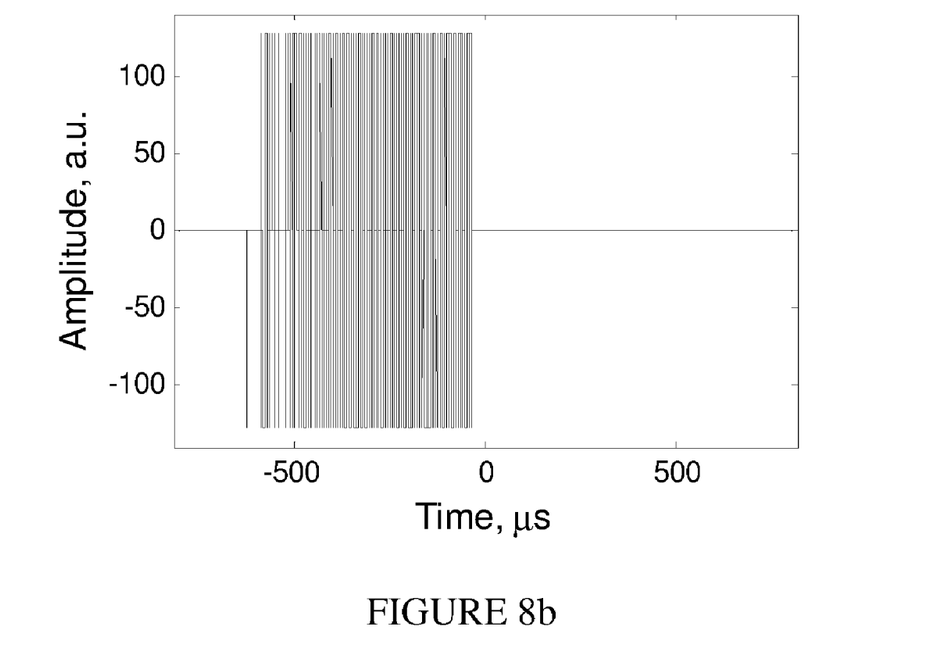
Figure 8C:
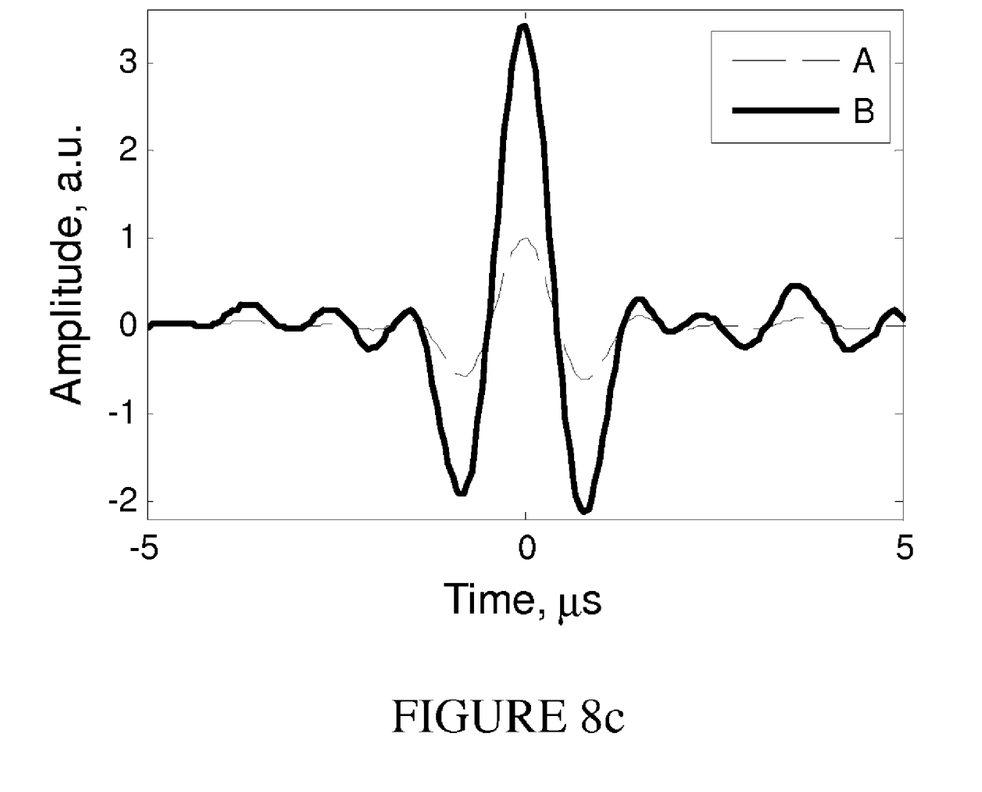

The method of the invention can be used in association with the above-described ternary mode. In the ternary mode, the zero value is assigned to a weak signal, which limits the influence of noise in the experimentally determined impulse responses. FIG. 8a shows an example of time-reversed pseudo-impulse response for one radiating transducer. FIG. 8b shows the associated ternary signal. FIG. 8c shows that ternary mode does not alter the waveform while significantly increasing the amplitude.

Figure 9:
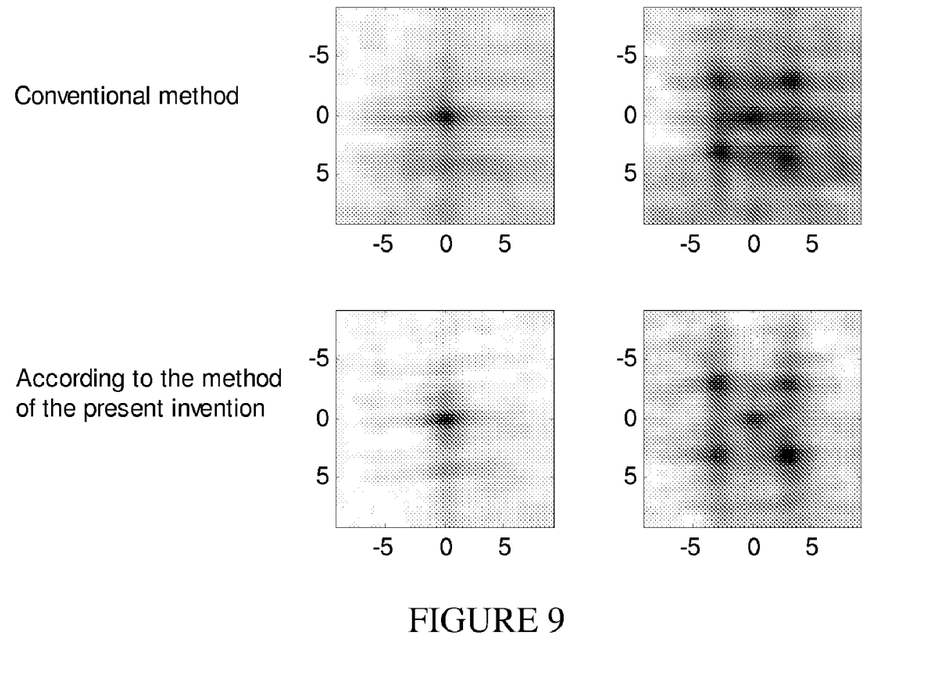
FIG. 9 illustrates spatial distributions of amplitude at time of focusing for a single focus (left) and for five foci (right) patterns. Results shown on the upper row are obtained with conventional methods, while those on the bottom row are obtained according to the method of the present invention. Axis units are in mm; and finally

FIG. 9 shows a spatial distribution of amplitude at time of focusing for a single focus (left column) and for a five foci pattern (right column) obtained using three channel time reversal system. First row presents results obtained with conventional method while results shown on the second row are obtained with a method of the present invention and show a better localization of the focused acoustic waves.

Figure 10:
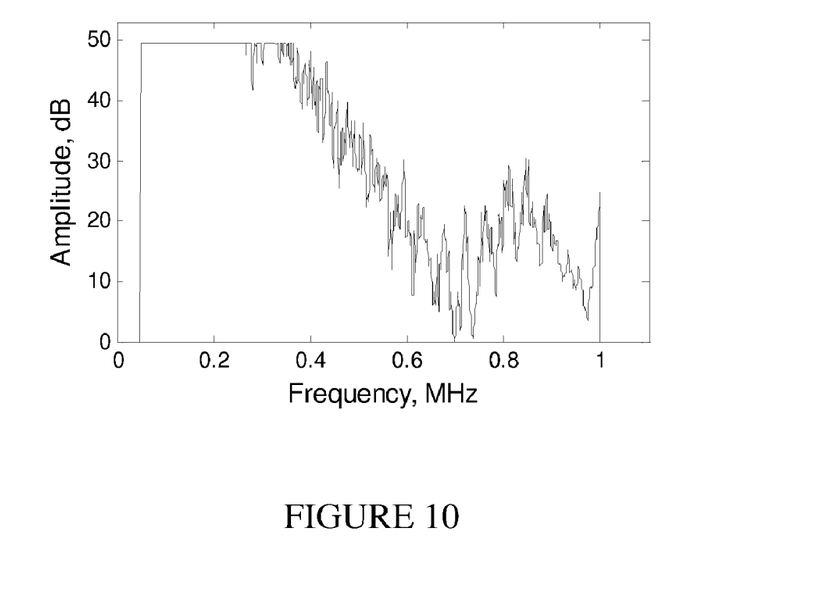
FIG. 10 shows a portion of the frequency response of a filter used according with the second aspect of the invention.

Finally, FIG. 10 shows a part of the frequency response of a filter designed according to the second aspect of the invention. This filter is created using the method of amplitude modulation discussed above. The flatness of the frequency response graph in the low frequencies seen in FIG. 10 is caused by the presence of a threshold.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A time-reversal method of focusing acoustic signals at a desired location in a media comprising steps as follows:
    (a) providing at least one radiating transducer adapted to emit acoustic signals to said media, said radiating transducer driven by a control system,
    (b) providing a sensor at said desired location to record response signals resulting from said acoustic signals arriving to said location in said media from said radiating transducer, said sensor connected to said control system to transmit said response signals thereto,
    (c) emitting an acoustic signal from said radiating transducer,
    (d) recording a response signal by said sensor,
    (e) computing a spectrum-adjusted signal based on said emitted and recorded signals, said spectrum-adjusted signal including attenuated spectral components with high amplitude and amplified spectral components with low amplitude, leading to flattening of the spectra of said signal and widening of its frequency band,
    (f) emitting said spectrum-adjusted signal from said radiating transducer,
    (g) recording a spectrum-adjusted response to said spectrum-adjusted emitted signal by said sensor,
    (h) computing a pseudo-impulse response from said spectrum-adjusted received and radiated acoustic signals,
    (i) time-reversing said pseudo-impulse response, and
    (j) storing said time-reversed signal for subsequent application thereof to said radiating transducer to provide focusing of acoustic signals at said desired location.

2. The method as in claim 1, wherein said step (e) is accomplished by modifying the sweep rate of a frequency sweep signal while keeping the signal amplitude constant.

3. The method as in claim 2, wherein said sweep rate at a given frequency is selected to be proportional to the square root of the power spectrum density of said response signal.

4. The method as in claim 1, wherein said step (e) is accomplished by modifying the amplitude of a linear frequency sweep signal while keeping its sweep rate constant.

5. The method as in claim 4, wherein said amplitude of the spectrum-adjusted signal is selected to be inversely proportional to the square root of said power spectrum density of said response signal.

6. The method as in claim 1, wherein said emitted acoustic signals are signals with orthogonal frequency content, whereby more than one radiating transducer can be provided with a dedicated respective emitted signal at the same time.

7. A time-reversal method of focusing acoustic signals at a desired location in a media comprising steps as follows:
    (a) providing at least one radiating transducer adapted to emit acoustic signals to said media, said radiating transducer driven by a control system,
    (b) providing a sensor at said desired location to record response signals resulting from said acoustic signals arriving to said location in said media from said radiating transducer, said sensor connected to said control system to transmit said response signals thereto,
    (c) emitting an acoustic signal from said radiating transducer,
    (d) recording a response signal by said sensor,
    (e) computing a spectrum-adjusted signal based on said emitted and recorded signals,
    (f) emitting said spectrum-adjusted signal from said radiating transducer,
    (g) recording a spectrum-adjusted response to said spectrum-adjusted emitted signal by said sensor,
    (h) computing a pseudo-impulse response from said spectrum-adjusted received and radiated acoustic signals,
    (i) time-reversing said pseudo-impulse response, said time-reversing including a ternary transformation of the time-reversed signal, and
    (j) storing said time-reversed signal for subsequent application thereof to said radiating transducer to provide focusing of acoustic signals at said desired location.

* * * * *